United States Patent [19]
White

[11] Patent Number: 5,400,476
[45] Date of Patent: Mar. 28, 1995

[54] APPARATUS AND METHOD FOR CONTROLLING DRAFT UNIFORMITY IN TEXTILE SLIVER

[75] Inventor: Homer S. White, Durham, N.C.

[73] Assignee: Myrick-White, Inc., Durham, N.C.

[21] Appl. No.: 273,736

[22] Filed: Jul. 12, 1994

[51] Int. Cl.$^6$ .................. D01H 5/72; D01H 5/74; G01N 21/01; G01B 11/00

[52] U.S. Cl. .................. 19/239; 19/150; 19/159 R; 19/159 A; 19/243; 356/386; 250/561

[58] Field of Search .............. 356/375, 386; 280/561, 280/571; 19/159 R, 150, 15 T, 236, 242, 243, 239, 115 A, 0.23

[56] References Cited

U.S. PATENT DOCUMENTS

| | | | |
|---|---|---|---|
| 2,959,279 | 11/1960 | Krafft et al. | 19/159 R X |
| 3,345,700 | 10/1967 | Kalwaites | 19/150 |
| 3,744,915 | 7/1973 | Sick | 356/386 X |
| 4,201,476 | 5/1980 | Musto et al. | 356/386 |
| 4,402,609 | 9/1983 | Fetzer et al. | 356/386 X |
| 4,827,141 | 5/1989 | Zwirn | 250/561 X |
| 4,929,843 | 5/1990 | Chmielewski, Jr. et al. | 250/561 |
| 5,233,728 | 8/1993 | Whiteley et al. | 19/159 R |
| 5,247,173 | 9/1993 | Benchetrir et al. | 250/561 X |
| 5,274,884 | 1/1994 | Demuth et al. | 19/159 A X |

FOREIGN PATENT DOCUMENTS 62057938A 9/1985 Japan.

*Primary Examiner*—John J. Calvert
*Attorney, Agent, or Firm*—Olive & Olive

[57] ABSTRACT

The present invention provides a drafting apparatus and method having a plurality of pairs of rollers which pairs are each driven in the same rotational direction and have silver contact points oriented along a common straight line. Sliver is fed to the primary rollers through a trumpet guide connected to a strain gage to determine the size of incoming silver and adjust the draft ratio accordingly to equalize the output silver weight. A silver presence and position detecting device operative on a reflected signal is provided adjacent the output of silver, which sends a signal through a computer to adjust the speed of the silver take up apparatus.

14 Claims, 7 Drawing Sheets

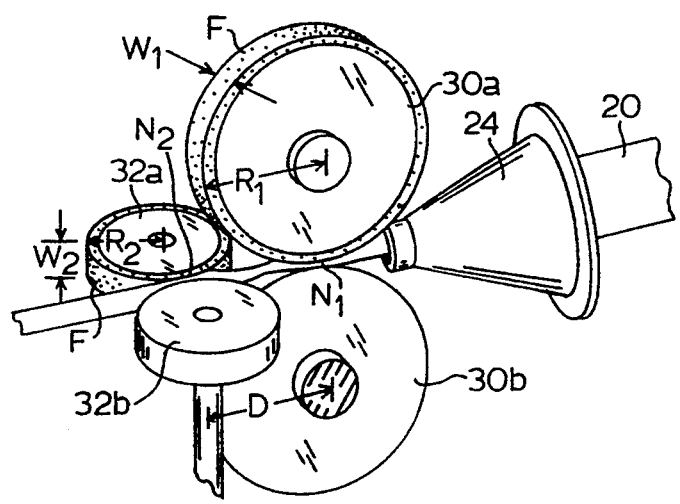
FIG. 7
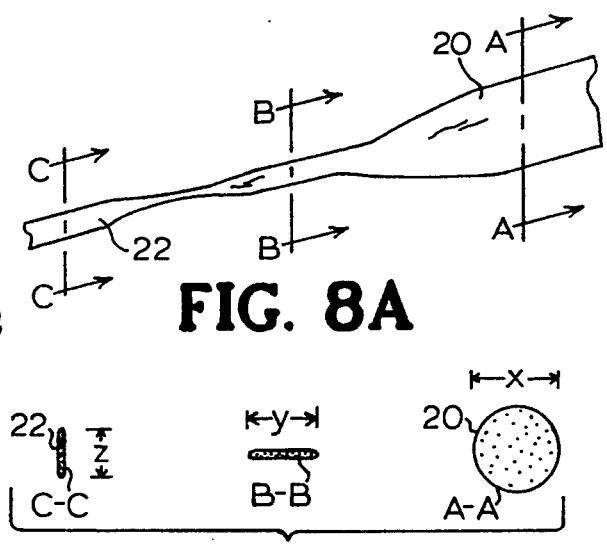
FIG. 8A
FIG. 8B
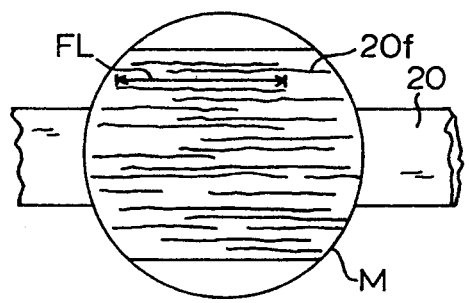
FIG. 9
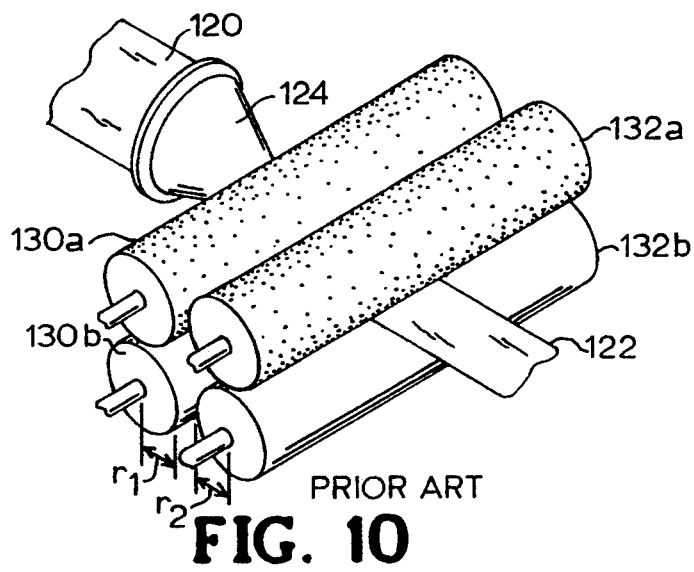
FIG. 10 PRIOR ART

APPARATUS AND METHOD FOR CONTROLLING DRAFT UNIFORMITY IN TEXTILE SLIVER

FIELD OF THE INVENTION

This invention relates to equipment and methods for drafting textile silver, and particularly to equipment and methods for drafting textile silver having relatively short filament length.

BACKGROUND OF THE INVENTION

Textile fibers are processed through a series of steps for conversion from the bale to the finished yarn or thread (hereafter referred to as yarn). Fiber from the bale is opened and cleaned and formed into a feed mat which is introduced into a carding machine. Here the fiber is further cleaned and straightened by the carding process and a thin web of the fibers is produced. The web is compressed widthwise to form a silver and the next step involves drawing or drafting the silver so as to increase its length and decrease its diameter. This drafting step decreases the weight of silver per unit length prior to the twisting or spinning steps which typically occur next in the production of yarn.

Certain fibers, particularly cotton fibers, are limited in the fiber length from one (1) to one and one-half (1½) inches and are typically one and one-eighth (1⅛) inches, in length. The ultimate strength of a yarn made up of many fibers depends on the frictional force between adjacent fibers acting to prevent tension applied to the yarn from pulling the fibers apart in the lengthwise direction. Thus, the strength of the yarn relies upon the character of the fiber surface (coefficient of friction), the force pressing adjacent fibers together (degree of twist) and the length of contact between adjacent fibers.

At the stage of drafting silver prior to beginning to twist the silver into yarn, the twist is negligible and so the inter-fiber force is minimal. Therefore the strength of the silver is dependent primarily on the coefficient of friction and the length of contact between adjacent fibers.

Drafting is the operation of extending the silver by driving a secondary pair of opposed silver conveying rollers which are downstream of a draft zone somewhat faster than a primary pair of opposed silver conveying rollers which are upstream of the draft zone. In the prior art drafting operations and equipment, control of relative silver weight per unit length from section to section of a silver was difficult, and breakages of the silver, requiring a rethreading of the equipment, occurred frequently.

The design of a drafting mechanism (known as a draw box) involves two basic decisions namely what should be the diameter of the rollers and what should be the spacing between the rollers. Since it is generally considered desirable to position rollers close together to maintain control of the silver, the question of roller diameter becomes the major decision. The optimum spacing of the rollers is considered to be in the range of 1½ times the fiber length extending between the primary and the secondary roller/silver nip points. It is further accepted textile theory that a roller set having relatively large diameter rollers is preferred because large diameter rollers provide a shallower entry angle and a longer contact with the silver being drawn. However, making rollers larger in diameter, according to conventional design, requires greater spacing. Therefore, the two preferences of closer spacing and larger diameters are somewhat contradictory. The novel principles embodied in the present invention enable the machine designer to significantly overcome this conflict.

U.S. Pat. No. 4,823,597 for a SLIVER MEASURING APPARATUS and U.S. Pat. No. 4,947,947 for a SLIVER MEASURING APPARATUS WITH OVERLOAD RELIEF, issued to the present inventor describe apparatus incorporating a funnel guide through which the silver passes and which mounts on a plate having a strain gage. The apparatus determines the relative bulk of the silver by its resistance to passage through the funnel. The resultant strain gage output signal is used to indicate the weight per unit length of silver based on which the draft ratio can be regulated. The teachings of the '597 and '947 patents are to be deemed incorporated herein by reference.

U.S. Pat. No. 2,975,501 to Whitmore discloses a roller arrangement in which a second pair of rollers is oriented substantially perpendicular to a first pair of rollers.

A further aspect of the present invention involves an improved non-contacting silver position detection unit. One prior device used to detect the silver position without contacting the silver requires use of a pair of parallel-mounted signal emitter-photosensitive cells connected to a logic device to determine silver presence in a target range. A second known device for the same purpose uses a plurality of such photocells and detectors mounted in a planar array to define a larger target zone. Neither of the mentioned prior silver detection devices have the advantages of the present invention.

It is therefore an object of this invention to provide an improved draft apparatus in which the distance between the nips of sequential roller sets is minimized.

It is a further object of this invention to provide an improved draft apparatus with improved means for controlling the weight per unit length of the silver being processed.

It is an additional object of this invention to provide an improved draft apparatus able to produce a substantially uniform drawn silver product.

Other objects and advantages will be more fully apparent from the following disclosure and appended claims.

SUMMARY OF THE INVENTION

A textile silver drafting apparatus typically processes silver through a set of primary rollers which rotate at a first speed and then through a set of secondary rollers which rotate at a second speed, the second speed being somewhat faster than the first speed. The invention disclosed herein provides a textile silver drafting apparatus in which the secondary roller set is located substantially closer to the primary roller set than was previously possible. This relative positioning in combination with other features of the invention, achieves an improved control of the uniformity of drafting. The configuration enabling this close positioning provides for both primary and secondary rollers to be narrow in comparison to their respective diameters and the secondary roller set to be oriented perpendicular to the orientation of the primary roller set. In this manner, the plane which includes both the secondary roller axes can be positioned less than one secondary roller radius plus one primary roller radius from the plane which includes the primary roller axes.

A further feature of the invention is the incorporation of a reflected beam scanning device which detects the height position of silver exiting from the drafting apparatus relative to an ideal height position and adjusts the speed of take-up in response thereto. The draft ratio between the primary and secondary roller speed is automatically adjusted according to the pressure on an input funnel, or trumpet, as described in U.S. Pat. Nos. 4,823,597 and 4,947,947 discussed above.

BRIEF DESCRIPTION OF THE DRAWINGS

FIG. 7 is a perspective view of the apparatus of FIG. 3 with the draft rollers of the invention positioned in close proximity to each other.

FIG. 8A is a perspective view of a textile silver as compressed by the apparatus of the invention, but shown with the rollers removed for clarity.

FIG. 8B illustrates a series of sections A—A, B—B and C—C as taken in FIG. 8A.

FIG. 9 is a view of a segment of textile silver with a portion magnified to illustrate the relationship of individual fibers.

FIG. 10 is a perspective view of a draw box of the prior art having substantially long draft rollers.

DETAILED DESCRIPTION OF THE INVENTION

Figure 1:
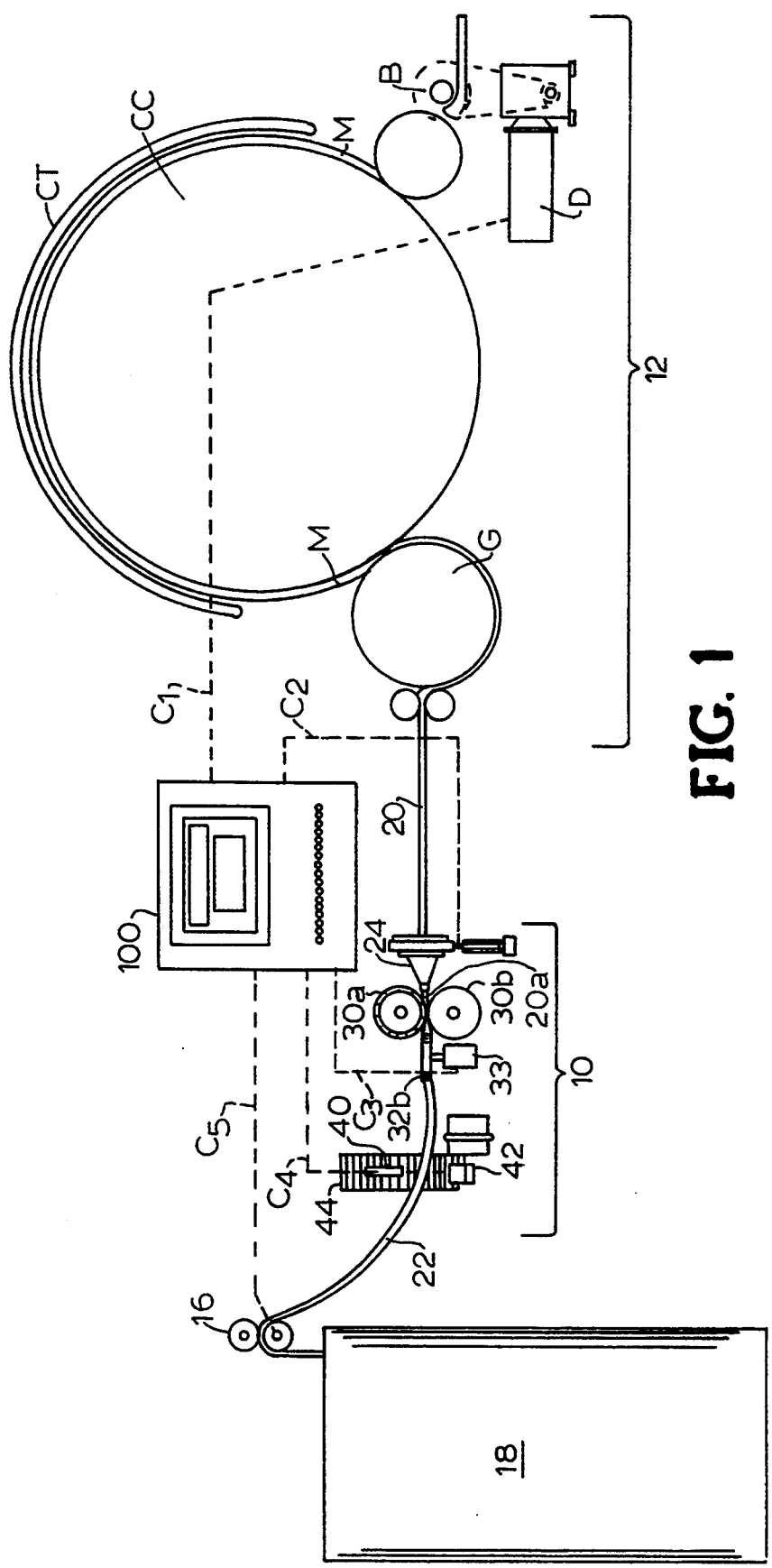
FIG. 1 is a schematic elevation view of a silver production machine including a carding machine and a drafting apparatus of the invention.

A typical, schematically represented drafting system in which silver is processed from carding machine 12 to receiving can 18 through the invention draw box 10 is illustrated in FIG. 1. The term "draw box" refers generally to that part of a drafting machine in which silver is run through a set of primary draft rollers at a first speed and through a set of secondary draft rollers at a second, faster speed so as to stretch or draw the silver. Fiber web 20 is supplied from carding machine 12. A variable speed drive motor D feeds a supply of randomly oriented fibers to carding roll E by means of feed roll B. Carding cylinder CC and top CT act to orient and spread the fibers to form a fiber web M which is subsequently removed by doffer G. The carded fiber web 20 passes from carding machine 12 through a trumpet 24 where it is compressed into silver 20A to be processed through draw box 10, and then proceeds as drawn silver 22 over driven rolls 16 to be coiled into rotating receiving can 18. The draw box 10 shown in FIG. 1 is that of the present invention, however, the overall system shown is applicable to a prior art draw box as seen in perspective in FIG. 10. Connective cables $C_1$, $C_2$, $C_3$, $C_4$ and $C_5$ connect various portions of the drafting system to controlling computer 100. Cable $C_1$ transmits a signal used to control the speed of drive motor D. Cable $C_2$ transmits input signals from a strain gage which measures deflection of trumpet 24. Cable $C_3$ transmits a signal to control and modulate the speed of secondary draft rollers 32a, 32b. Cable $C_4$ transmits a signal generated by emitter/detector 40 in correspondence with the presence, absence and strength of the light beam received by emitter/detector 40. Cable $C_5$ carries a signal to control the operative speed of driven rolls 16.

Figure 2:
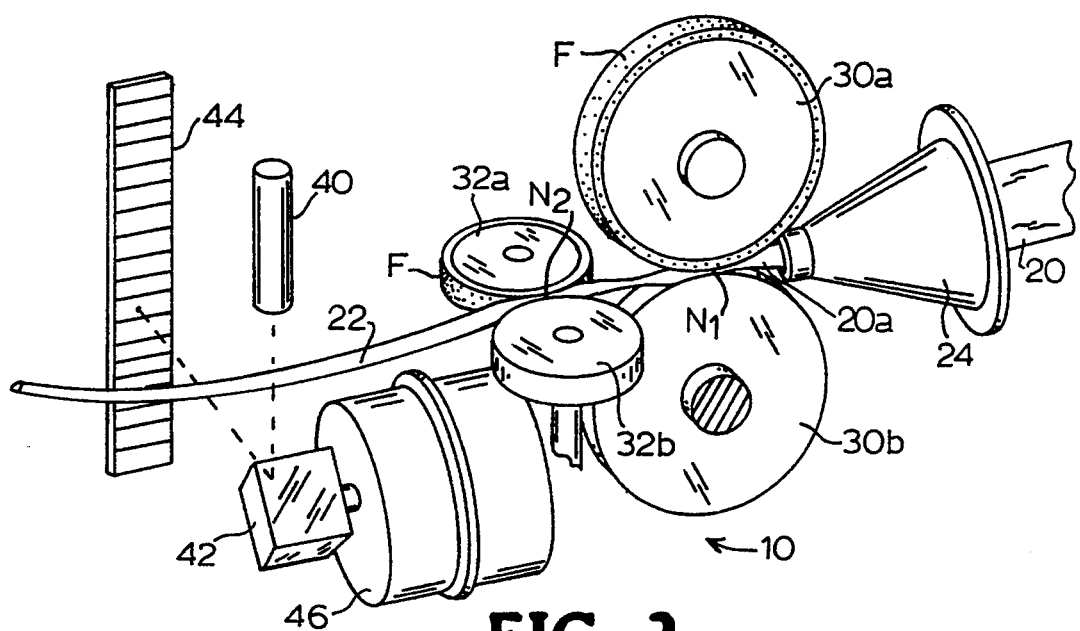
FIG. 2 is a perspective view of the drafting apparatus of the invention.

FIG. 2 portrays the apparatus of the present invention in perspective view. Particular novel features of the invention draw box apparatus 10 include the draft rollers being substantially narrower than their respective diameters and the secondary rollers 32a, 32b being oriented in a plane perpendicular to the plane of the primary rollers 30a, 30b. This relative perpendicularity enables the secondary rollers 32a, 32b to be positioned closer to the primary rollers 30a, 30b than would be possible if their respective axes were parallel, as is common. In essence, the invention configuration permits the two roller sets to nest into one another. The invention also provides a drawn silver position detector system comprising signal emitter/detector 40, rotating four-sided mirror 42 and prismatic reflector 44, all of which are described in detail below.

FIG. 10 represents a typical draw box of the prior art. Combed silver 120 is delivered to the draw box through trumpet guide 124. Conventional primary rollers 130a, 130b and secondary rollers 132a, 132b are long in comparison to their respective diameters, as illustrated. With this arrangement, the shortest distance possible between the nip points of the primary and secondary rollers is the sum of the radii r1, r2 of one roller of each set plus a small space. Note that while the rollers are all illustrated as being similar in diameter, rollers of different diameters have been known to have been used. The output result is shown as drawn silver 122 of considerably smaller cross section than that of combed silver 120. It has been recognized in the industry that since silver is constituted as a loose fiber bundle, the rollers tend to bear strongly on the center area of the silver and to a significantly lesser degree at its edges. Under the drafting arrangement of FIG. 10, the amount of stretch imparted near the center of silver 120 is typically greater than the stretch near the edges of silver 120 because of the relative bulk of silver near its center, and this differential will in turn affect yarn integrity.

Figure 3:
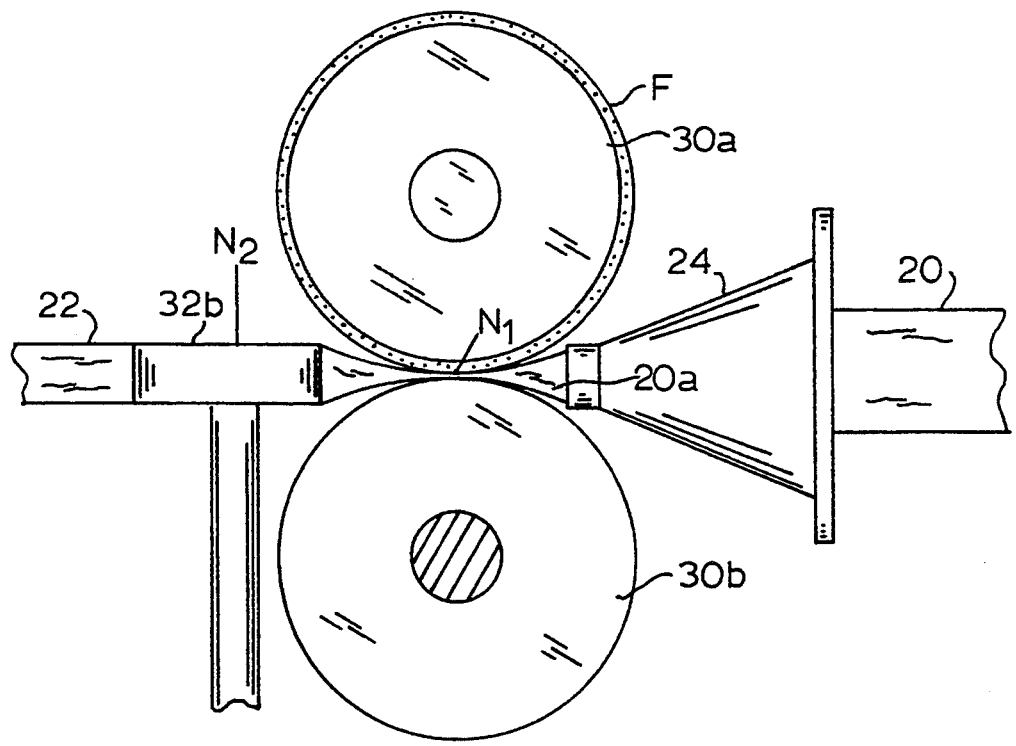
FIG. 3 is a side elevation view of a trumpet guide and the draw box of the invention and with the mounting plate for the trumpet guide removed for purposes of illustration.
Figure 4:
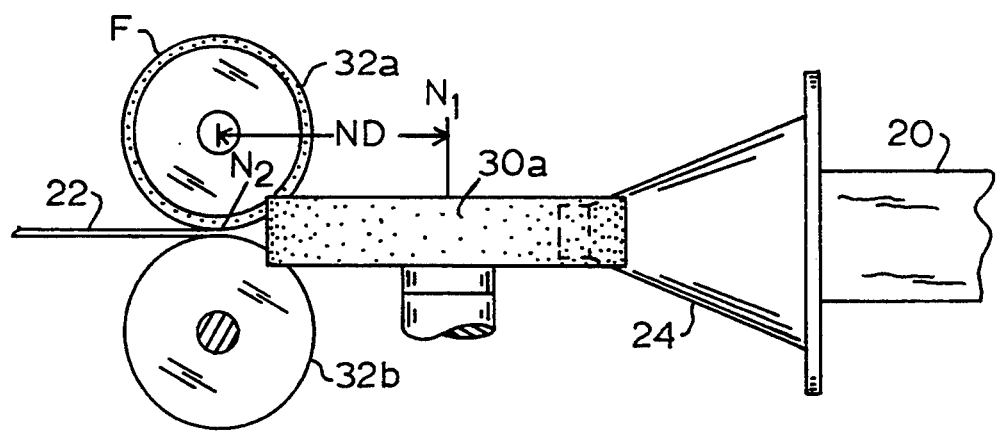
FIG. 4 is a top plan view of the apparatus shown in FIG. 3.

The apparatus of the present invention is shown in various views and in various forms in FIGS. 2–7, each employing identical parts numbering. Referring now to FIGS. 3 and 4, a funnel shaped input trumpet guide 24 is positioned so as to compress web 20. Trumpet 24 forms and directs silver 20A to the contacting surfaces of primary rollers 30a, 30b which pull and flatten the silver 20 and pass it to secondary rollers 32a, 32b. According to the illustrations, lower primary roller 30b and left secondary roller 32b are each driven by a power source (not shown), and upper primary roller 30a and right secondary roller 32a are coupled mechanically or by friction drive means to each respective primary and secondary roller so as to rotate at the same speed but in the opposite rotational direction. In the preferred embodiment, primary roller 30b is driven from a constant speed drive and secondary roller 32b is driven by a variable speed A/C motor responsive to frequency change. One roller of each set (illustrated as rollers 30a, 32a) is illustrated as being covered with a resilient, frictional material F such as, e.g. polyurethane. While the primary rollers are shown to be identical to each other in size, as are the secondary rollers, different diameter rollers would be applicable to the principles of the invention.

As carded silver 20A emerges from trumpet guide 24, it is seen to contact rollers 30a, 30b essentially at nip point N1 (FIG. 3). Continuing in the process, silver 20 next passes between rollers 32a, 32b and is compressed and driven at nip point N2. The nip distance ND (FIG. 4) from nip point N1 to nip point N2 can be effectively minimized by the configuration of the invention wherein the drafting rollers are relatively thin and the secondary drafting rollers are oriented in a plane perpendicular to the plane of the primary rollers.

According to common practice, secondary rollers 32a, 32b are driven at a speed greater than that of primary rollers 30a, 30b in order to impart a degree of stretch to the silver being processed. A secondary roller surface linear speed in the range of 1.5 to 2.5 times the surface linear speed of the primary rollers is typical.

As will be apparent to those skilled in the art, the axis of trumpet guide 24 and a tangent at each of nip points N1 and N2 are arranged along a common straight line. Upon initial threading, a silver end passed through trumpet guide 24 to primary rollers 30a, 30b will follow automatically to secondary rollers 32a, 32b. When a silver is being processed through the draw box 10, the portion of silver 20A passing between primary rollers 30a, 30b is squeezed flat in a horizontal plane and the portion passing between secondary rollers 32a, 32b becomes flat in a vertical plane (see FIGS. 8A, 8B). As shown in cross section in FIG. 8B, the width Y of silver 20 at section B—B is considerably smaller than the diameter X at section A—A because of compression by trumpet guide 24 and the pressure applied by rollers 30a, 30b. The width Z of silver 20 at section C—C is less than the width Y at section B—B by reason of secondary rollers 32a, 32b operating at a faster speed than primary rollers 30a, 30b, thus stretching silver 20. Therefore, a further optional embodiment, shown by comparison of FIGS. 3 and 4, is to configure secondary rollers 32a, 32b narrower than the width of primary rollers 30a, 30b.

Drafting operations are primarily applicable to carded fibers which are first laid together as a web, then gathered to form a silver and later twisted. The fiber length of cotton is typically about 1⅛ inches. It is recognized that in order to keep good control over the drafting of silver, it is desirable to have the distance between the nip points of successive roller sets as short as possible. A roller spacing from one nip point to the next nip point is preferably about 1½ times the fiber length. The invention observes that if the draft rollers are made small in diameter, the distance between the nip points of primary and secondary sets of rollers can also be made small. However, small rollers have certain limitations which may introduce operating drawbacks, such as the effective length of silver with which contact is made, the angle at which the silver enters the rollers and minor variations which may occur in the operating speed.

FIG. 9 shows a segment of silver 20, a portion of which is shown enlarged under magnifying glass M. Within the frame circle of magnifier M, a number of substantially parallel fibers 20f are illustrated in detail, each fiber having a typical fiber length FL. As it is shown, the relative position of individual fibers 20f varies, with the first end of one being adjacent to the middle or opposite end of others.

The relative positioning of the primary and secondary rollers shown in FIGS. 2-6 allows some moderate space between the primary and secondary roller sets, even though their respective peripheries are moderately overlapping. In FIG. 7, the spacing between primary roller nip point N1 and secondary roller nip point N2 has been reduced to approximately a minimum distance D. It has been determined that the minimum distance D achievable with a draw box having perpendicularly oriented roller sets can be mathematically derived from the formula:

$$D = \sqrt{W_2 \times R_1 - W_2^2/4} + \sqrt{W_1 \times R_2 - W_1^2/4}$$

where: D = minimum distance between the axes of the roller sets
$W_1$ = width of the primary rollers
$R_1$ = radius of the primary rollers
$W_2$ = width of the secondary rollers
$R_2$ = radius of the secondary rollers as shown in FIG. 7. This formula has been determined to be applicable as long as the width of the rollers in each set is less than the radius of the rollers in each respective opposite set. The arrangement of relatively narrow, perpendicularly oriented draft roller sets thus achieves closer nip point distances and greater silver draft control. The formula above could be modified to a more complex form to cover a configuration wherein the rollers of the primary set or the rollers of the secondary set are of different diameters.

Figure 5:
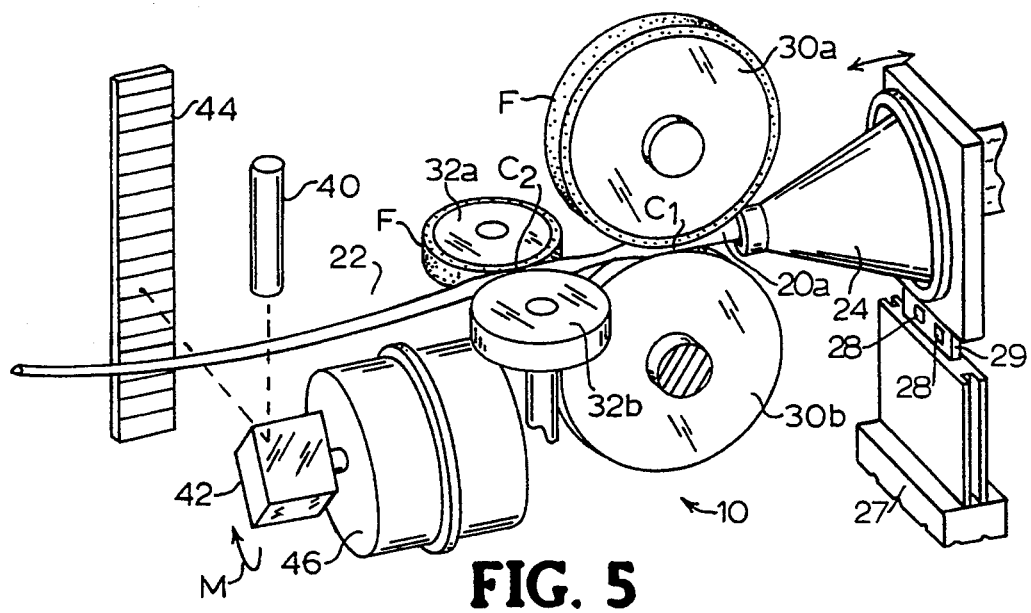
FIG. 5 is a perspective view of the draft apparatus of the invention showing the trumpet supported on a mounting plate with a schematically represented strain gage.
Figure 6:
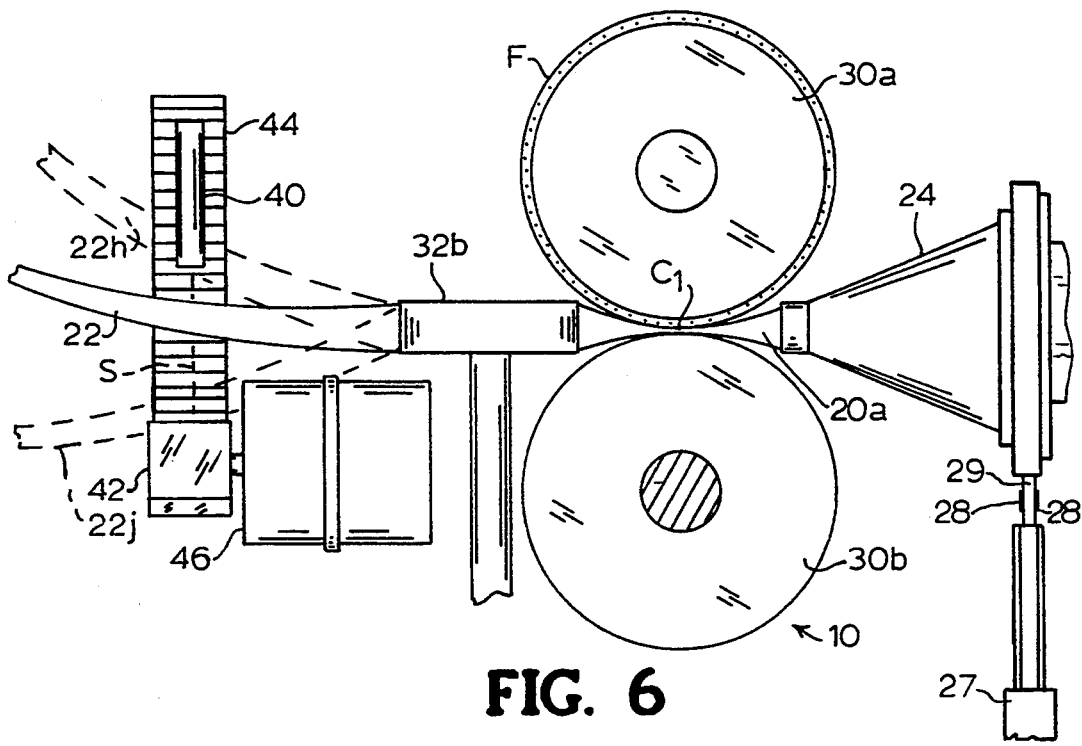
FIG. 6 is a side elevation view of the apparatus shown in FIG. 5.

The apparatus of the invention further incorporates trumpet guide support 26 as illustrated in FIGS. 5 and 6 and which may be of the type described in applicant's prior U.S. Pat. No. 4,823,597. Support 26 is rigidly mounted to a schematically represented base, or machine frame 27, and in a reduced section 29, is somewhat flexible in order to permit a slight degree of movement as the pressure of compressing incoming carded web 20 through trumpet guide 24 changes. Support 26 may be mounted in any position relative to the trumpet guide 24, i.e. it may be above, below or to the side of trumpet guide 24. When the reduced section 29 of the support 26 flexes, its movement is detected by one or more strain gages 28, whose strain creates control voltages transmitted through cable $C_2$ to a computer 100 which in response generates a second signal through cable $C_3$ to appropriately control the draft ratio between the primary and secondary roller sets (FIG. 1) all as more fully described in the '597 patent. A further control signal generated by computer 100 in response to input from strain gages 28 and transmitted through cable $C_1$ acts to modulate the speed of driver motor D. The invention recognizes that since silver control signals from trumpet guide 24 are obtained from a point upstream of the drafting zone, correction in draft ratio can be effective. Therefore, the control signals for draft roll motor 33 are generated and transmitted by computer 100 at a rate of up to 120 signals per second. The signals reach and correct the speed of motor 33 in time for the silver segment on which the strain gage measurement was taken to be drawn at the correct ratio to make the output substantially uniform from segment to segment. Computer 100 also collects and averages the silver weight information and sends signals to modulate the speed of drive motor D at a rate of about 10 signals per second. The speed corrections to drive motor D are of a smaller magnitude than those for draft roll motor 33 and are based on average readings over time. Thus, only if continued indications of silver weight derivation from a target range occur does the feed roll B receive a correcting instruction, and to a less severe degree. This process to determine silver unit weight, and control draft ratio is more fully described in the referred to U.S. Pat. Nos. 4,947,947 and 4,823,597, the teachings of which are incorporated herein by reference.

A further system which is integrated in the invention apparatus acts to detect the vertical position of the drawn silver at a position downstream from the draft rollers, as shown in FIGS. 5 and 6. This silver position detection system provides advantages over certain of the prior known systems in that no physical contact with silver occurs during the detection process. Under ideal conditions, defined in terms of drive speed, silver weight and tension, the drawn silver 22 will follow a substantially horizontal path outwardly from the nip point of secondary rollers 32a, 32b. When the drive speed of rollers 32a, 32b is relatively low compared to the silver tension caused by the speed of the take-up can 18 mechanism, the line 22h along which the silver travels (FIG. 6) will be above horizontal. When the drive speed of rollers 32a, 32b is relatively high compared to the silver tension, the line 22j along which the silver travels will drop to a low position.

Figure 11A:
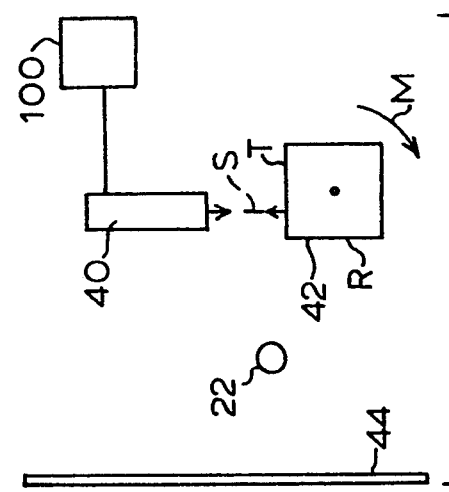
FIGS. 11A–11F comprise a series of illustrations showing end elevation views of the scanner device of the invention at sequential positions in the rotational cycle of its four-sided mirror and showing the corresponding path of the emitted and reflected light beams used to determine silver position.
Figure 11B:
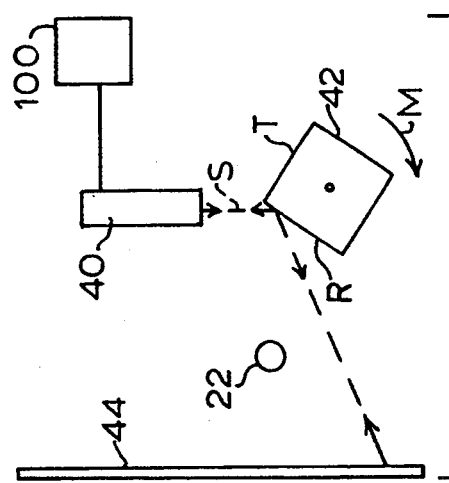
Figure 11C:
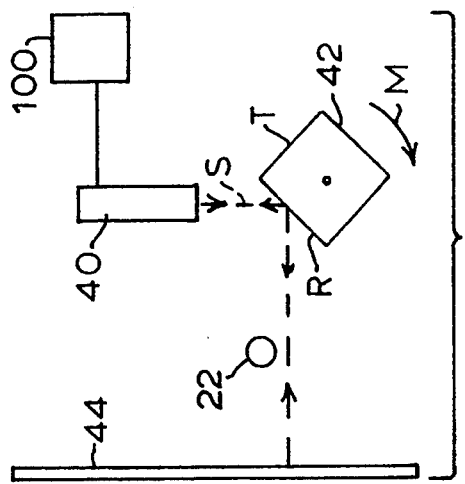
Figure 11D:
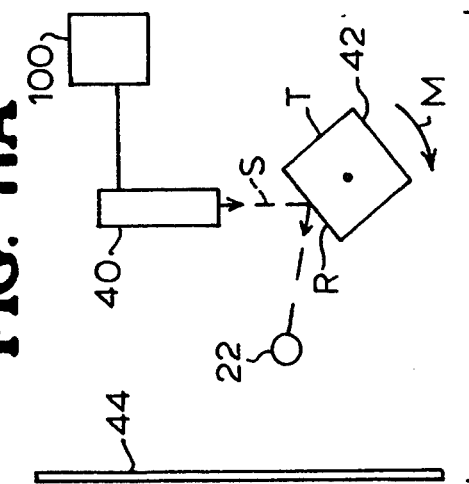
Figure 11E:
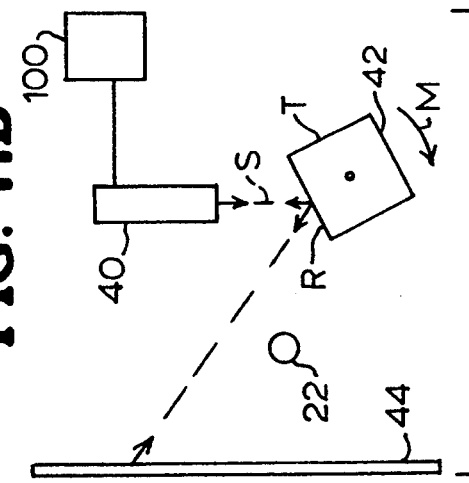
Figure 11F:
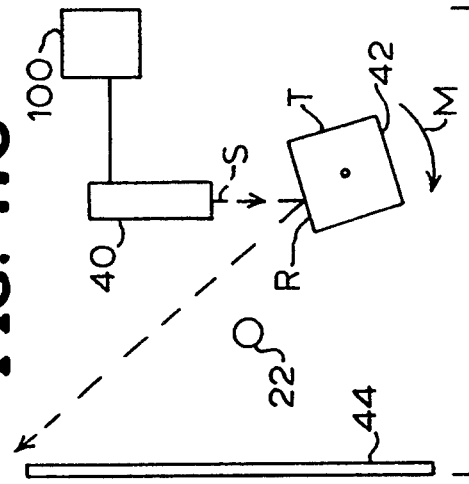

Signal emitter/detector 40, in the preferred embodiment, is capable of both generating an outgoing light signal in the infrared range and in response to receiving a reflected such signal generating a control signal sent to computer 100. The emitter/detector of the preferred embodiment is supplied by Omron Electronics as model number E3F-R2C4 and is equipped with a general purpose photoelectric cell. While the preferred embodiment employs an infrared frequency beam, the invention emitter/detector 40 is mounted so that its emitted infrared light signal S will perpendicularly contact side T of four-sided mirror 42 when the mirrored sides are oriented horizontally and vertically respectively (FIG. 11A). The perpendicular contact as illustrated in FIG. 11A causes a direct reflection pulse of short duration which is used by computer 100 as a cycle reference point. As four-sided mirror 42 is rotated by motor 46 in the direction indicated by arrow M, signal S contacts side R at different points because of the sequentially angled positions (FIGS. 11B–11F). Motor 46 includes means capable of producing an output signal indicative of the angular position of the rotating portion thereof. As each scan of four-sided mirror 42 is shown in sequential FIGS. 11B–11 F, the reflected signal S is moved in an arc from a downward angle from mirror side R (FIG. 11B) to prismatic reflector 44 through a horizontal position to an upward angle (FIG. 11E). As motor 46 rotates four-sided mirror 42 beyond the position indicated in FIG. 11E to the position shown in FIG. 11F, signal S is reflected offside R upwardly beyond prismatic reflector 44. In this rotational range, no reflected signal returns to emitter/detector 40 and a black image is processed by computer 100. Prismatic reflector 44 is comprised of a plurality of very small angularly oriented reflective surfaces causing signal S to be reflected back 180° from the direction from which received, regardless of angle of incidence. Highway signs and reflective tapes are typical examples of products using this type of prismatic reflector. Signal S reflects off four-sided mirror 42 to prismatic reflector 44, which is able to reflect signal S along its line of incidence back to mirror 42 and then to emitter/detector 40. The length of prismatic reflector 44 is set to be greater than the useful range of positions of silver 22 and short enough so that signal S may pass the lower and upper ends of reflector 44 without contacting. At the position shown in FIG. 11 D, signal S contacts silver 22, causing signal S to be effectively absorbed. This condition causes the computer 100 connected to emitter/detector 40, to recognize that the silver position has been found, and to respond accordingly as described with regard to FIGS. 5 and 6. Computer 100 sends a control signal to the take up can 18 drive via cable $C_5$ (FIG. 1 ). When drawn silver 22 is in its desired position as illustrated in solid lines in FIG. 6, no correction in speed is needed. When silver 22 assumes high position 22h, this indicates that a greater amount of tension is applied to silver 22 and the speed of receiving can 18 (FIG. 1) is decreased incrementally. The converse action is undertaken if silver 22 is detected to be in the low position, shown as 22j.

Figure 12A:
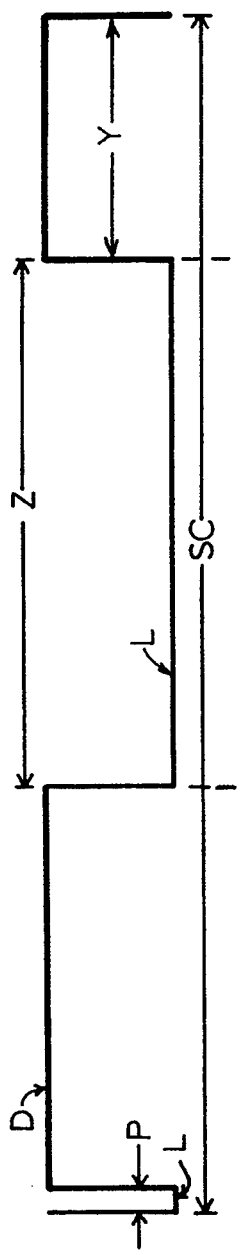
FIGS. 12A–12D comprise a series of graphical representations of the scanner signal which is developed in response to the reflected beam in differing conditions of silver position determination.

FIGS. 12A–12D comprise a series of typical signal reception patterns from computer 100 as the scanner system responds to a variety of silver position conditions. The drawn graphical line represents relative reflection, with flat upper portion D indicating no reflection and flat lower portion L indicating a reflection of signal detected. In FIG. 12A, the system is assumed to be operating without silver present. Starting from the left and proceeding in rotational direction M (FIGS. 11 A–11F), the first portion of reflection is one pulse P in width and occurs when signal S is reflected from side T of four-sided mirror 42 when oriented perpendicular to the path of signal S (see FIG. 11A). The next portion, marked D, indicates no signal detected by emitter/detector 40 and is occurring as signal S is reflected from side T and later from side R as mirror 42 rotates in a direction which will pass the ends of prismatic reflector 44 and thus will not reflect so as to be detected. Next, the signal reflects from side R of four-sided mirror 42 (FIG. 11B) and is reflected back from reflector 44 to emitter/detector 40 in an uninterrupted reflected zone Z. Last in the scan illustrated is the portion Y of the cycle when the signal reflects off four-sided mirror side R to pass the upper extreme of reflector 44. One complete scan SC of a side of mirror 42 is equal to 45 pulses the width of pulse P. Computer 100 compares an angular position signal from motor 46 with the reflected signal S to determine the angle of the reflected beam and the position of silver 22.

Figure 12B:
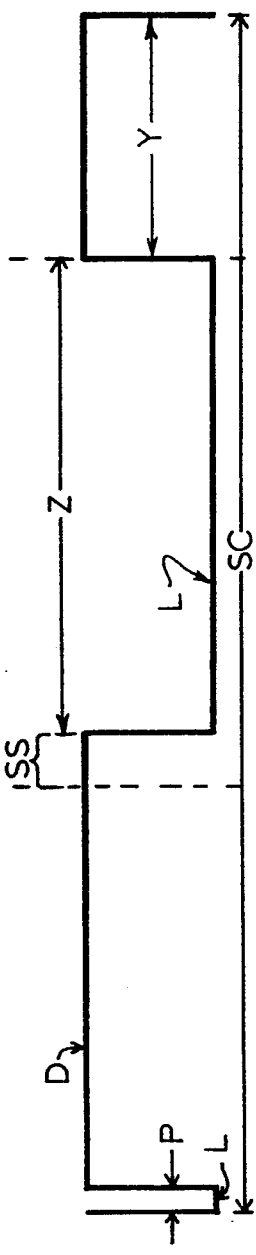

In FIG. 12B, silver is indicated to be present at the bottom portion of reflector 44. Its presence is determined by the initiation of reflectance being delayed by more than the time of one pulse P, shown as time span SS.

Figure 12C:
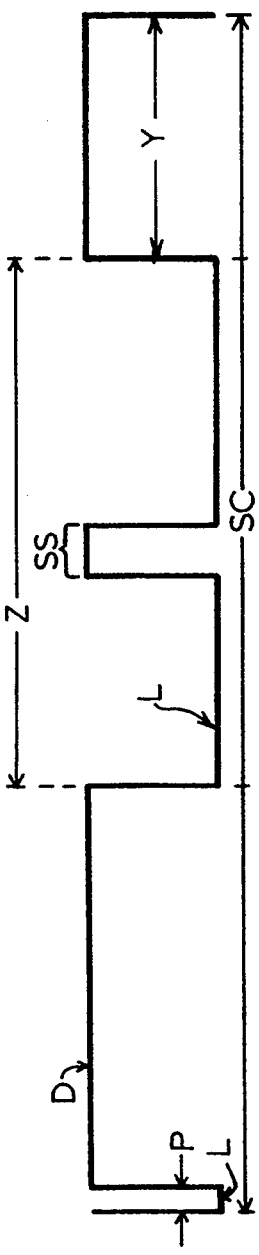

FIG. 12C portrays a condition in which the silver is detected as a segment of non-reflection approximately in the middle of the normal reflective zone Z. The width of silver as detected is SS.

Figure 12D:
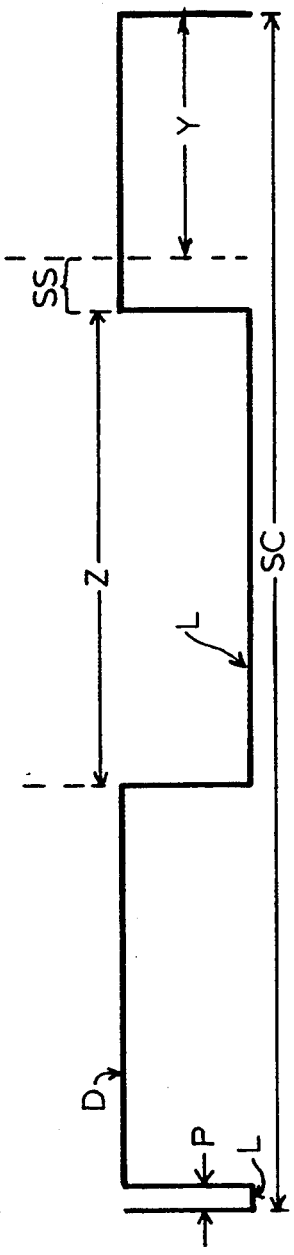

FIG. 12D illustrates the opposite condition to that of FIG. 12B, wherein silver appears as portion SS near the end of the reflective zone Z, thus terminating the reflectance sooner than otherwise would occur.

The computer program is established to allow in all conditions for a deviation of one pulse without indicating a silver presence. For a single pulse change in position, the program will adjust its expected start point for each event accordingly. The program also allows the machinery to continue its normal operation with the silver assumed in its last sighted position for four further scan time cycles before shutting the machinery down, thus being useful to detect a missing silver as well as a silver out of the desired range of position.

Alternatively, separate means to transmit and detect a radiant signal may be employed provided that the signal is moved across a field through which a silver or other strand passes transversely such that at least one point in a motion cycle of the signal intercepts the strand.

Thus, the invention as disclosed herein provides a novel apparatus and method for controlling silver uniformity through a combination of minimizing draw distance between roller contact points, varying draw ratio according to the silver weight as determined by resistance against a trumpet guide and varying take-up speed in response to the output angle of the silver from the draft rollers. The silver position detection scanner unit may be similarly applied to various continuous strand processes, such as that of extrusion.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A silver draw box, comprising:
   (a) a first pair of silver drafting rollers positioned to receive input silver and having respective parallel axes and driven at a first selected speed and in a selected direction;
   (b) said first pair of rollers being operative to pressingly engage a silver passing therebetween at a first nip point;
   (c) a second pair of silver drafting rollers positioned to receive said input silver from said first pair of rollers and having respective parallel axes and driven at a second selected speed and in a same said selected direction as said first pair of drafting rollers;
   (d) said second pair of rollers being operative to pressingly engage a silver passing therebetween at a second nip point;
   (e) said second selected speed being greater than said first selected speed; and
   (f) said first and second pair of rollers being oriented with respect to each other such that a linear distance between said first nip point and said second nip point is less than a sum of radii of one roller of each of the first and second pair of rollers.

2. The silver draw box as claimed in claim 1 wherein the axes of said first pair of rollers reside in a plane which is oriented substantially perpendicular to a plane in which the axes of said second pair of rollers reside.

3. The silver draw box as claimed in claim 1 wherein the width of each roller of said first pair is less than the radius of each roller in said second pair and the width of each roller of said second pair is less than the radius of each roller in said first pair.

4. The silver draw box as claimed in claim 1, further comprising sensing means positioned so as to sense weight per unit length of the input silver and to generate a control signal in response thereto.

5. The silver draw box as claimed in claim 1, wherein said sensing means comprises a trumpet guide for compressing said silver as said silver passes through said trumpet guide and mounting detection means for developing said control signal indicative of weight per unit length of said silver dependent on resistance of said silver when passing through said trumpet guide.

6. A silver draw box apparatus, comprising:
   (a) a first pair of silver drafting rollers positioned with respective axes mutually parallel and driven at a first selected speed and direction for pressingly engaging a silver passing therebetween at a first nip point;
   (b) a second pair of silver drafting rollers positioned with respective axes mutually parallel and driven at a second selected speed and direction for pressingly engaging a silver passing therebetween at a second nip point;
   (c) said second selected speed of said second pair of silver drafting rollers being greater than said first selected speed of the first pair of rollers and the direction of the first and second rollers being identical;
   (d) said first and second pair of rollers being oriented with respect to each other such that a linear distance between said first nip point of said first pair of rollers and said second nip point of said second pair of rollers is less than a sum of radii of one roller of each of the first and second pair of rollers;
   (e) driven silver receiving means for withdrawing said silver discharged from said second pair of rollers for further processing and in the course of such withdrawal permitting said silver to travel as a strand along a path a portion of which is substantially horizontal and preferably at some predetermined elevation related to a longitudinal tension impressed thereon;
   (f) a scanner for detecting the elevation of said silver in the course of travel along said path, comprising:
      (i) a first signal source for generating and emitting a first beam-like signal in a selected direction along a substantially straight line;
      (ii) a first constant speed rotating reflector positioned for reflecting said first signal received from said first signal source and cause said first signal to sweep in a vertical plane which intersects the path of said silver;
      (iii) a second fixed reflector positioned such that said strand is located substantially between said first and second reflectors and for receiving and reflecting said first signal to said first reflector along substantially an identical line from which said first signal was received by said second reflector;
      (iv) detector means positioned proximate said first signal source for receiving said reflected signal from said first reflector and for generating a second signal in response thereto;

(v) a second signal source associated with said first reflector and operative to produce a third signal indicative of an angular position thereof; and (vi) computer means connected to said detector means and said second signal source for receiving and processing said second and third signals and for developing a fourth control signal to regulate the path of said strand when said first signal is interrupted by said strand at other than said predetermined elevation.

7. A silver draw box apparatus, comprising:

(a) a first pair of silver drafting rollers configured with respective axes mutually parallel and driven at a selected speed and direction for pressingly engaging a silver passing therebetween;

(b) a second pair of silver drafting rollers configured with respective axes mutually parallel and driven at a selected speed and direction for pressingly engaging a silver passing therebetween;

(c) the direction of the first and second pair of drafting rollers being identical the selected speed of said second pair of drafting rollers being greater than the selected speed of said first pair of drafting rollers;

(d) a linear distance between a nip point of said first pair of drafting rollers and a nip point of said second pair of drafting rollers being less than a sum of radii of one roller of each of the first and second pair of rollers;

(e) sensing means positioned adjacent a supply of said silver for evaluating weight per unit length of said silver prior to said silver entering said first set of rollers;

(f) driven silver receiving means for withdrawing said silver discharged from said second pair of rollers for further processing and wherein said silver travels as a strand along a path a part of which is substantially horizontal and at a predetermined elevation related to longitudinal tension impressed thereon; and (g) a scanner for detecting a position of said silver in the course of travel along said path, comprising:

(i) a first signal source for generating and emitting a signal in a selected direction along a substantially straight line;

(ii) a first rotatable constant speed driven reflector positioned for reflecting said first signal received from said first signal source and causing said first signal to sweep in a vertical plane intercepting the path of said silver;

(iii) a second fixed reflector positioned such that said strand is located substantially between the second reflector and the first reflector and for receiving and reflecting said first signal to said first reflector along substantially an identical line from which said first signal was received by the second reflector;

(iv) detector means positioned proximate said first signal source and for receiving said reflected signal from said first reflector and for generating a second signal in response thereto;

(v) a second signal source associated with said first reflector and operative to produce a third signal indicative of an angular position of said first reflector; and (vi) computer means connected to said sensor means for receiving and processing said second and third signals developing a fourth control signal to regulate the path of said strand in absence of said strand being intercepted by said first signal at said predetermined elevation.

8. The silver draw box as claimed in claim 7, wherein said sensing means comprises a trumpet guide for compressing said silver as said silver passes therethrough and motion detection means for generating a signal responsive to resistance of said silver passing through said trumpet guide.

9. The silver draw box as claimed in claim 7, wherein said first reflector comprises a rotatably driven cube member mounted for rotation about an axis which intersects two opposed sides of said cube member and having reflective surfaces on the four remaining sides thereof.

10. The silver draw box as claimed in claim 7 wherein a minimum linear distance between said first nip point and said second nip point is determined by the formula:

$$D = \sqrt{W_2 \times R_1 - W_2^2/4} + \sqrt{W_1 \times R_2 - W_1^2/4}.$$

11. A method for drawing a textile silver, comprising the steps of:

(a) passing said silver linearly between a first pair of rollers rotating about substantially parallel axes and pressingly engaging said silver therebetween at a first peripheral nip point;

(b) providing a second pair of rollers rotating about substantially parallel axes residing in plane which is substantially perpendicular to a plane occupied by the axes of said first pair of rollers, passing said sliver linearly between said second pair or rollers and pressingly engaging said silver therebetween at a second nip point, positioning said second pair of rollers with the second nip point being linearly aligned with the first nip point of said first pair of rollers;

(c) rotating said second pair of rollers at a higher speed than the speed of said first pair of rollers during passage of said silver therebetween; and positioning said second pair of rollers closer to said first pair of rollers than a distance equal to the radius of one of said first pair of rollers plus the radius of one of said second pair of rollers.

12. The method for drawing a textile silver as claimed in claim 11, further comprising the step of passing said silver through a weight per unit length detector apparatus adapted to adjust the speed ratio between said first pair of rollers and said second pair of rollers in response to the detected weight per unit length of said silver.

13. The method for drawing a textile silver as claimed in claim 11, further comprising the step of withdrawing said silver from said second pair of rollers into a driven silver receiving device, detecting without contact the position of said silver at a location beyond said second pair of rollers and adjusting the operative speed of said silver receiving device based on said detected silver position.

14. The method for drawing a textile silver as claimed in claim 12, further comprising the steps of withdrawing said silver from said second pair of rollers with a driven silver receiving device, detecting the position of said silver at a location beyond said second pair of rollers and adjusting the speed of said silver receiving device based on said detected silver position.

* * * * *

UNITED STATES PATENT AND TRADEMARK OFFICE
CERTIFICATE OF CORRECTION

PATENT NO. : 5,400,476            Page 1 of 2
DATED      : March 28, 1995
INVENTOR(S): Homer S. White It is certified that error appears in the above-indentified patent and that said Letters Patent is hereby corrected as shown below:

Correct the spelling of "silver" to read --sliver-- in the following places:

In the abstract: lines 4, 7, 8, 9, 11 and 12.

Column 1, lines 19, 20, 36, 37, 39, 42, 43, 45, 48, 49, 50, 57 and 65.

Column 2, lines 9, 11, 14, 23, 24, 25, 27, 31, 37, 42, 50, 54.

Column 3, lines 3, 11, 32, 37, 47, 51, 56, 59.

Column 4, lines 2, 3, 33, 48, 49, 50, 52, 56, 57, 64, 66.

Column 5, lines 16, 18, 29, 35, 38, 39, 43, 47, 50, 57, 60.

Column 6, lines 1, 2, 5, 40, 67.

Column 7, lines 5, 9, 15, 18, 24, 25, 28, 29, 30, 34, 35, 38 (twice)

Column 8, lines 16, 18, 21, 25, 27, 28, 30, 34, 39, 61, 62, 67.

Column 9, lines 2, 4, 9, 13, 15, 19, 23, 26, 28, 29, 30, 41, 42, 43, 47, 49, 50, 56, 65.

Column 10, lines 1, 6, 8, 10, 12 (twice), 15, 16, 17, 18, 21, 23, 26, 30, 40, 41, 43, 48, 56.

Column 11, lines 11, 12, 15, 16, 19, 30, 31 (twice), 33, 34, 36, 40, 49.

Column 12, lines 3, 5 (twice), 9, 15, 23, 25, 34, 41, 46, 49, 51, 52, 54, 55, 56, 58 (twice), 60, 62, 63, 64, 65, 66.

Column 7, line 15, Correct "derivation" to read --deviation-- (applicant error).

Column 8, line 1, correct "offside" to read -- off side--

UNITED STATES PATENT AND TRADEMARK OFFICE
CERTIFICATE OF CORRECTION

PATENT NO. : 5,400,476
DATED : March 28, 1995
INVENTOR(S) : Homer S. White

It is certified that error appears in the above-indentified patent and that said Letters Patent is hereby corrected as shown below:

Column 12, line 33, "or" to read --of--.

Signed and Sealed this

Twentieth Day of June, 1995

Attest:

BRUCE LEHMAN

Attesting Officer

Commissioner of Patents and Trademarks